(12) United States Patent
Krueger et al.

(10) Patent No.: US 6,214,043 B1
(45) Date of Patent: *Apr. 10, 2001

(54) RELEASABLE HANGER FOR HEART VALVE PROSTHESIS LOW PROFILE HOLDER

(75) Inventors: Kurt D. Krueger, Stacy; Kimberly A. Anderson, Eagan; Guy P. Vanney, Blaine; Thomas F. Hinnenkamp, White Bear Lake, all of MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/962,752

(22) Filed: Nov. 3, 1997

Related U.S. Application Data

(63) Continuation of application No. 08/719,192, filed on Sep. 24, 1996, now abandoned, which is a continuation-in-part of application No. 08/449,145, filed on May 24, 1995, now Pat. No. 5,578,076.

(51) Int. Cl.⁷ ..................................................... A61F 2/24
(52) U.S. Cl. .......................................................... 623/2.11
(58) Field of Search .............................. 623/2, 900, 2.11; 606/1

(56) References Cited

U.S. PATENT DOCUMENTS

| | | | |
|---|---|---|---|
| 3,828,787 | 8/1974 | Anderson et al. | 128/303 |
| 3,860,005 | 1/1975 | Anderson et al. | 128/303 |
| 4,655,218 | 4/1987 | Kulik et al. | 128/321 |
| 4,679,556 | 7/1987 | Lubock et al. | 128/303 |
| 4,683,883 | 8/1987 | Martin | 128/303 |
| 4,755,181 | 7/1988 | Igoe | 623/2 |
| 4,865,600 | 9/1989 | Carpentier et al. | 623/2 |
| 4,932,965 | 6/1990 | Phillips | 623/2 |
| 5,041,130 | 8/1991 | Cosgrove et al. | 623/2 |
| 5,236,450 | 8/1993 | Scott | 623/2 |
| 5,350,420 | 9/1994 | Cosgrove et al. | 623/2 |
| 5,370,685 | 12/1994 | Stevens | 623/2 |
| 5,403,305 | 4/1995 | Sauter et al. | 606/1 |
| 5,443,502 | 8/1995 | Caudillo et al. | 623/2 |
| 5,476,510 | 12/1995 | Eberhardt et al. | 623/2 |
| 5,480,425 | 1/1996 | Ogilive | 623/2 |
| 5,531,785 | 7/1996 | Love et al. | 623/2 |
| 5,571,215 | 11/1996 | Sterman et al. | 623/66 |
| 5,578,076 | 11/1996 | Krueger et al. | 623/2 |
| 5,628,789 | 5/1997 | Vanney et al. | 623/2 |
| 5,735,894 | * 4/1998 | Krueger et al. | 623/2 |
| 5,776,187 | * 7/1998 | Krueger et al. | |
| 5,824,068 | 10/1998 | Bugge | 623/2 |

FOREIGN PATENT DOCUMENTS

| | | |
|---|---|---|
| 1 008 937 | 7/1984 | (SU) . |
| 1 690 738 A1 | 11/1991 | (SU) . |
| 1 690 739 A1 | 11/1991 | (SU) . |
| WO 91/17720 | 11/1991 | (WO) . |
| WO 94/18881 | 9/1994 | (WO) . |
| WO 95/15715 | 6/1995 | (WO) . |
| WO 95/17139 | 6/1995 | (WO) . |

* cited by examiner

*Primary Examiner*—Bruce Snow
(74) *Attorney, Agent, or Firm*—Hallie A. Finucane, Esq.; Westman, Champlin & Kelly, P.A.

(57) ABSTRACT

A device for engaging a heart valve prosthesis during implantation includes a hanger and a holder. The holder includes a distal engaging surface adapted for engaging the heart valve prosthesis. The hanger is used to suspend the prosthesis in packaging and may be used to manipulate the prosthesis during implantation.

19 Claims, 15 Drawing Sheets

RELEASABLE HANGER FOR HEART VALVE PROSTHESIS LOW PROFILE HOLDER

This is a Continuation application of U.S. Ser. No. 08/719,192, filed Sep. 24, 1996, now abandoned which is a Continuation-In-Part of U.S. Ser. No. 08/449,145, filed May 24, 1995, now U.S. Pat. No. 5,578,076, issued Nov. 26, 1996.

FIELD OF THE INVENTION

The present invention relates to devices for implanting heart valve prostheses. More specifically, the invention relates to a releasable hanger for a low profile holder which holds a heart valve prosthesis during implantation.

BACKGROUND OF THE INVENTION

Holders for holding and supporting heart valve prostheses during shipping and implantation are known. They are used for positioning, holding, supporting and presenting the valve during surgery. U.S. Pat. No. 3,828,787, issued Aug. 13, 1974, to Anderson et al., entitled COLLET FOR HOLDING HEART VALVE, shows a heart valve holder carried on a distal end of an elongated handle. U.S. Pat. No. 4,932,965, issued Jun. 12, 1990, to Phillips, entitled ARTIFICIAL VALVE, AND NEEDLE AND SUTURE HOLDER AND METHOD OF USING SAME, shows another heart valve holder in which the valve is held against distal ends of a pair of elongated legs during implantation.

Traditionally, heart valve replacement surgery is an involved procedure in which a sternotomy or thoracotomy is performed and the chest cavity of the patient must be widely opened to provide access to the patient's heart. This provides a surgeon with direct, unobstructed access to the heart. However, this procedure requires a prolonged period to recover from the trauma suffered to the upper torso.

A minimally invasive procedure has been developed wherein open heart surgery is performed through small incisions which eliminate the need for a lateral sternotomy. This is described in International Publication No. WO 94/18881, entitled METHOD FOR PERFORMING THORASCOPIC CARDIAC BYPASS PROCEDURES and WO 95/15715, entitled DEVICES AND METHODS FOR INTRACARDIAC PROCEDURES. In this procedure, elongated tools are used to operate on the heart through the trocars. As discussed in Publication Nos. 94/18881 and 95/15715, this procedure can be used during heart valve replacement.

The trocar requires minimal rib spreading and does not involve the significant chest trauma associated with traditional open heart surgery. One advantage of this procedure is that the recovery period can be reduced significantly.

Heart valve prostheses are typically carried in packaging which are not designed for a low profile holder such as those which may be used to perform such minimally invasive surgery. For example, the packaging may include a collar which is adapted to receive a traditional (non-low profile) holder such that the holder and prosthesis are suspended from the collar in the packaging. Such a traditional holder may also be used during implantation and couples to an elongated handle. Unfortunately, low profile holder designs may not be compatible with the packaging used with traditional holders. Further, a low profile holder is not adapted for prosthesis implantation using traditional techniques.

SUMMARY OF THE INVENTION

An apparatus for engaging a heart valve prosthesis during implantation includes a hanger and a low profile holder. The low profile holder includes a coupling area and a distal engaging surface adapted for coupling to the prosthesis. The hanger is adapted for releasably coupling to the low profile holder. In one embodiment, the hanger is slidably coupled to the holder at a groove defined in the holder. Further, in one embodiment the hanger is adapted for suspension in packaging used to transport and store the heart valve prosthesis prior to implantation. In another embodiment, the hanger may be used in conjunction with the low profile holder to perform a traditional (i.e., non-minimally invasive) implantation while the low profile holder alone may be employed to perform minimally invasive heart valve replacement surgery.

DETAILED DESCRIPTION OF THE PREFERRED EMBODIMENTS

The invention relates to a device which is used to position a heart valve prosthesis during implantation. The implantation may be through minimally invasive surgery, performed through an incision smaller than that which is required for a sternotomy or thoracotomy, or using a more traditional implantation technique in which the axis of the valve is generally parallel with the axis of the handle to which it is attached. For purposes of this description of the invention, the device will be described generally with regard to its use with a bi-leaflet mechanical heart valve which has an annulus with a substantially annular aperture. Such a heart valve prosthesis is available from St. Jude Medical, Inc. of St. Paul, Minn. However, it will be understood that the invention is applicable to other types of heart valves as well.

The invention provides a hanger and holder for use with a heart valve prosthesis. The holder is preferably a low profile holder suitable for minimally invasive implantation.

Figure 1:
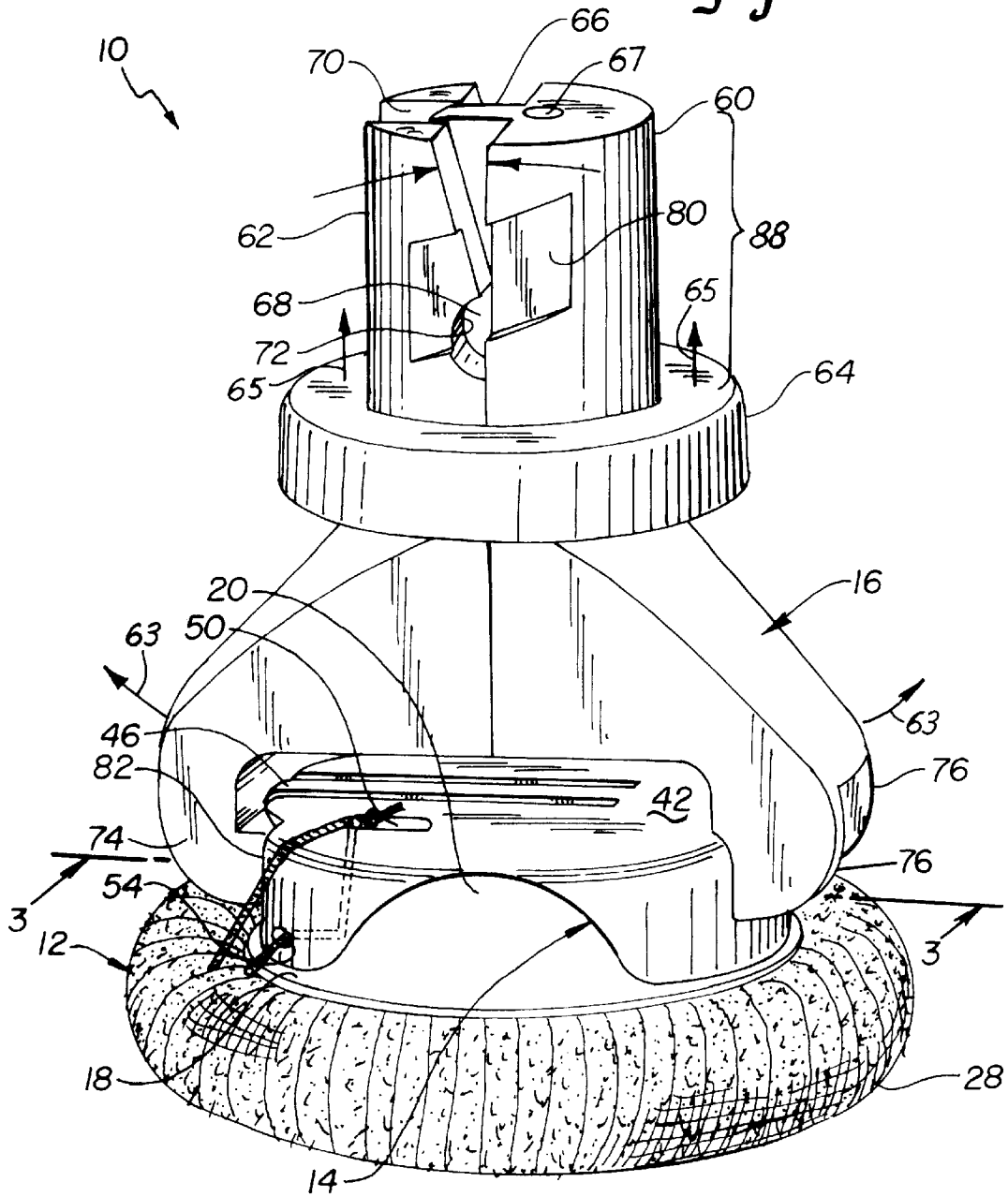
FIG. 1 is as perspective view of an assembly including a hanger and a low profile valve holder in accordance with one embodiment.
Figure 2:
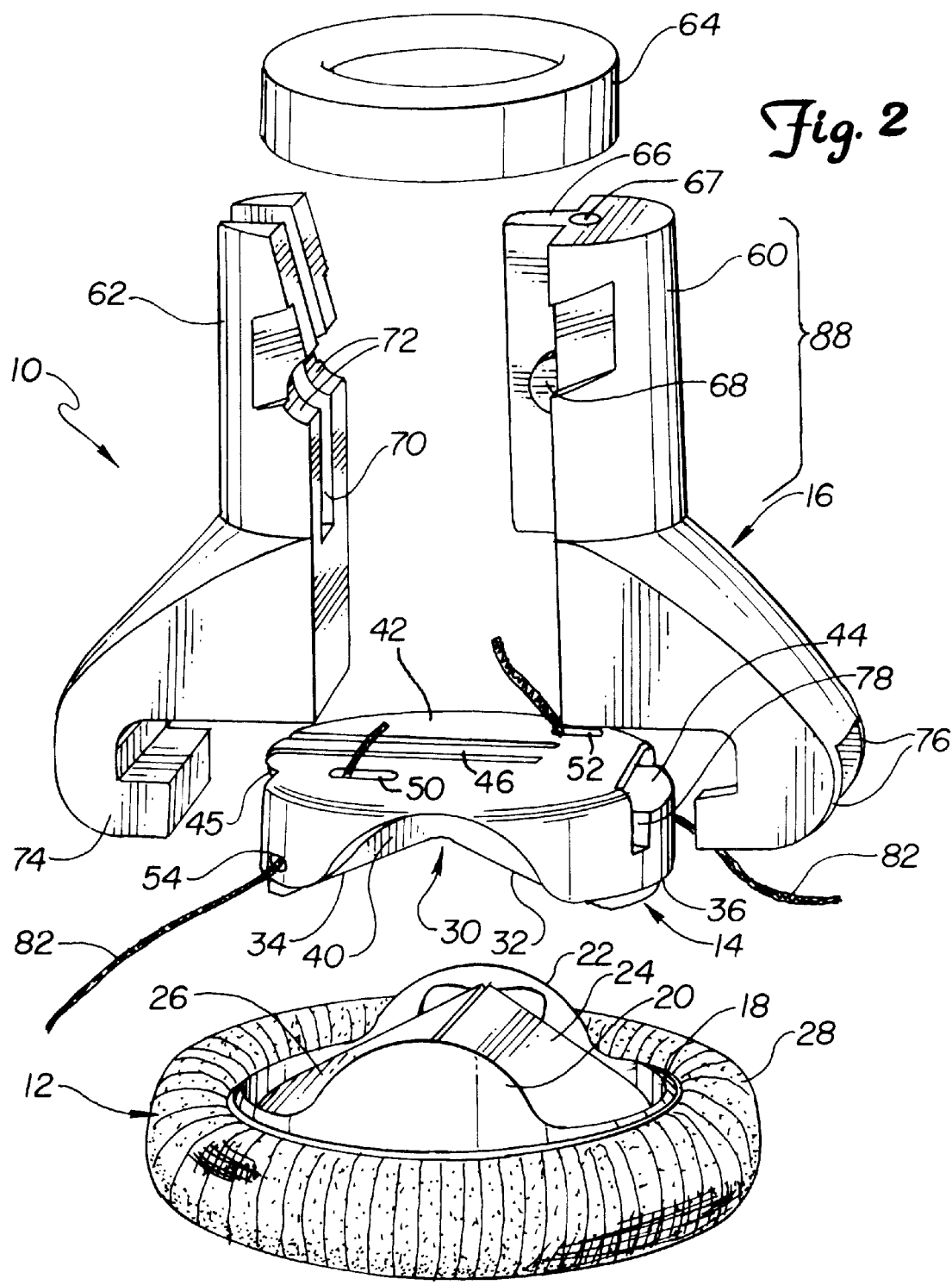
FIG. 2 is an exploded perspective view of the assembly of FIG. 1.

The hanger is adapted for suspension from packaging such as that used for shipment and storage of the prosthesis. The packaging may be of a standard configuration such that the assembly is retrofit to function with existing packaging. Further, the hanger may be used in conjunction with the holder to perform a traditional (non-minimally invasive) implantation in which the prosthesis is moved into position in the patient in a direction along the axis of the prosthesis. FIG. 1 is a perspective view and FIG. 2 is an exploded perspective view, respectively, of an assembly 10 which includes mitral heart valve prosthesis 12, heart valve holder 14 and hanger 16 in accordance with one embodiment. Valve 12 includes valve orifice 18 having leaflet pivot guards 20 and 22 which carry leaflets 24 and 26. A suture cuff 28 surrounds the outer radius of orifice 18.

Holder 14 includes distal surface 30 which provides leaflet conforming surfaces 32 and 34 adapted for receiving a proximal side of valve 12. A radial lip 36 extends around the outer circumference of distal surface 30 and conforms to valve orifice 18. Holder 14 includes pivot guard receiving portion 40 adapted for receiving pivot guards 20 and 22. Holder proximal surface 42 is a planar surface which is substantially parallel with the annulus of valve 12 and perpendicular to the axis of the hanger body 88. Surface 42 is positioned adjacent pivot guards 20 and 22 to provide an overall low profile to holder 14 as viewed from the side. Surface 42 overlies slot 44 and includes cantilever arm 46 which carries a tab (not shown). Surface 42 includes suture holes 50,52 and the outer radius of holder 14 includes suture holes 54.

Hanger 16 includes holder stems 60 and 62 and collar 64 which couples stems 60 and 62 when hanger 16 is assembled onto holder 14. Tab 66 extends from stem 60 throughout the length of hanger body 88 adjacent pivot 68. Stem 62 includes slot 70 for receiving tab 66 and pivot receptacle 72 for receiving pivot 68. Leg 74 of stem 62 fits in slot 45 of holder 14 and legs 76 of stem 60 fit in downward extensions 78 of slot 44. Hanger 16 is adapted for suspending holder 14 and valve 12 at notch 80 in packaging (not shown) during transportation and prior to implantation. Holder 14 is removed from hanger 16 by removing collar 64 as shown by arrows 65 from stems 60 and 62 such that stems 60 and 62 rotate about pivot 68 as shown by the arrows 63 in FIG. 1. Holder 14 is secured to valve 12 by sutures 82 which extend through holes 50 and 54 of holder 14 and through cuff 28 of valve 12.

During minimally invasive implantation, the surgeon removes assembly 10 from the packaging (not shown). Hanger 16 is removed from holder 14 by removing collar 64 in the direction shown by arrows 65 and squeezing the proximal end of hanger 16 together. This causes legs 74, 76 to pivot about pivot 68, thereby separating hanger 16 from holder 14. A handle is inserted into slot 44 and locked into place by a tab on cantilever 46. Leaflets 24 and 26 are protected within orifice 18 during insertion. The valve 12 is passed through the chest wall and is secured to the heart tissue annulus. After valve 12 is secured to the tissue annulus of the heart, holder 14 is then removed by cutting sutures 82 and removing holder 14 from the patient. Further, assembly 10 may be used for traditional implantation through a sternotomy or thoracotomy by using an elongated handle (not shown in FIGS. 1 and 2) which couples to hanger 16 at receptacle or bore 67 and extends in an axial direction with respect to the valve prosthesis.

Figure 3:
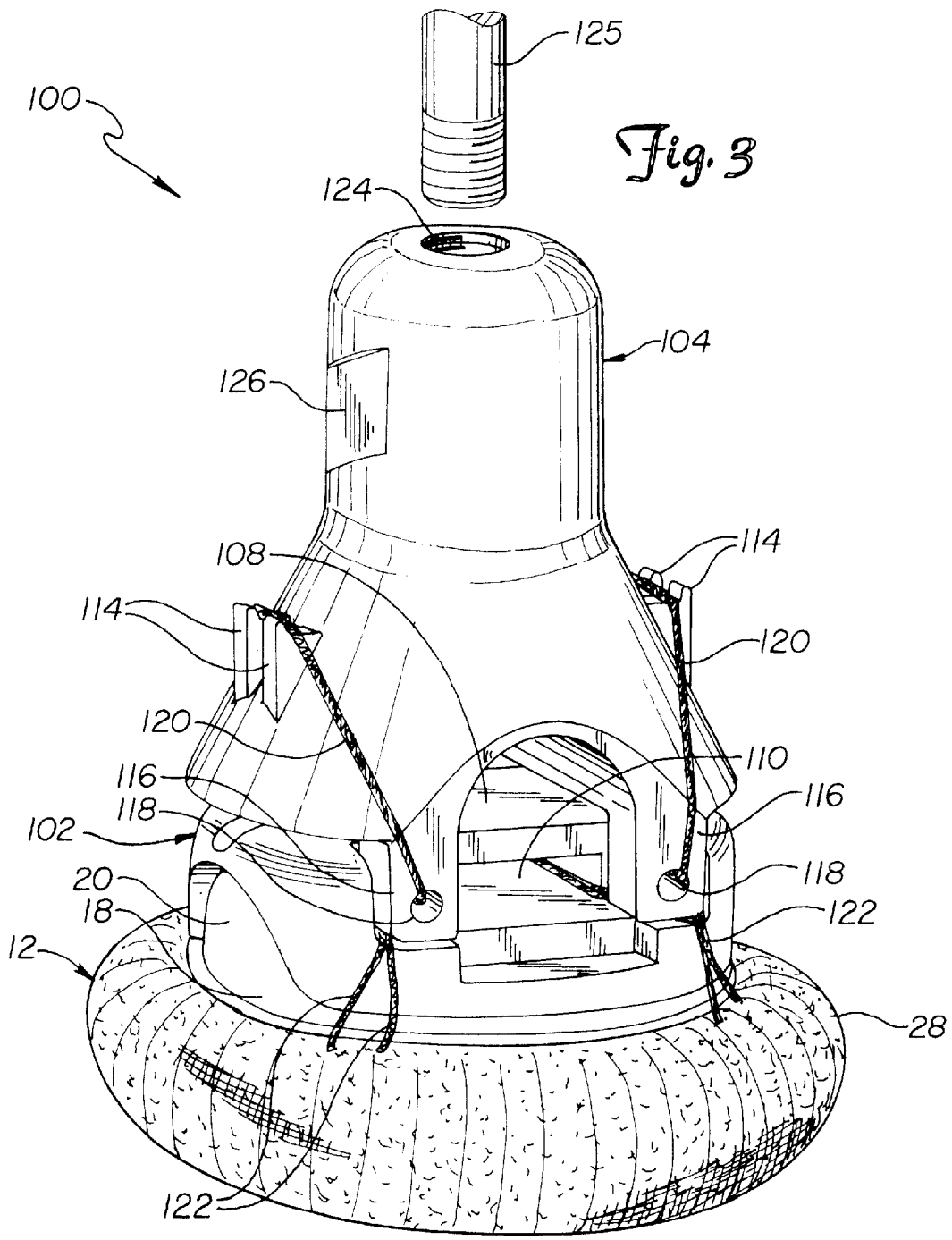
FIG. 3 is a perspective view of an assembly including a hanger in accordance with another embodiment.
Figure 4:
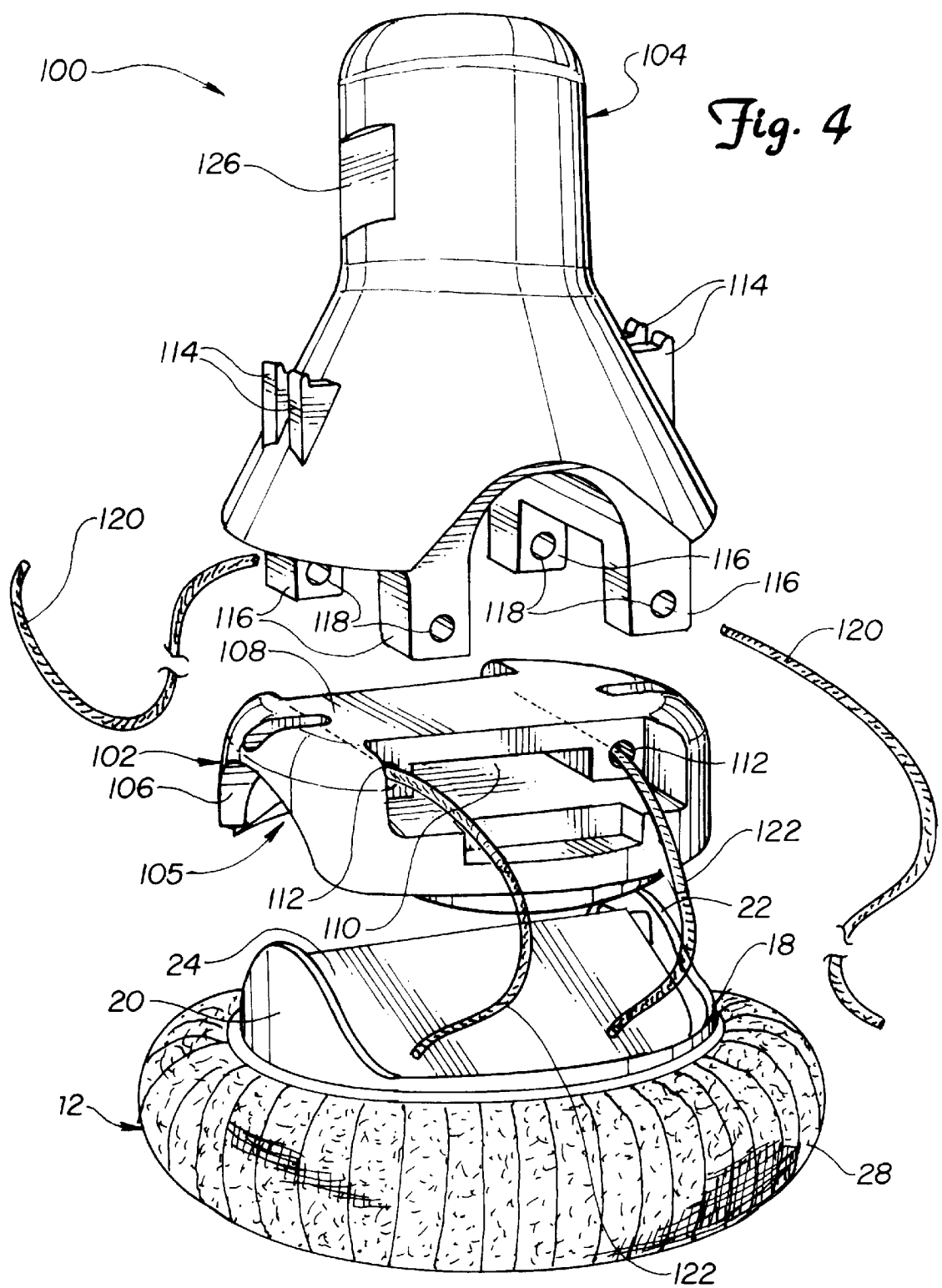
FIG. 4 is an exploded perspective view of the assembly of FIG. 3.

FIGS. 3 and 4 show a perspective view and an exploded perspective view, respectively, of assembly 100 in accordance with another embodiment. Assembly 100 includes holder 102 which couples to valve 12 and is supported by hanger 104 in a package (not shown). A distal engaging surface 105 of holder 102 is similar to surface 30 shown for holder 14 in FIGS. 1 and 2. Holder 102 includes pivot guard receiving portions 106 and proximal surface 108. A slot 110 and suture openings 112 extend through holder 102 perpendicular to the axis of valve 12.

Hanger 104 includes suture shoulders 114 and legs 116 having suture openings 118. Sutures 120 extend through holes 118 of hanger 104 and through holes 112 of holder 102 thereby securing hanger 104 to holder 102. Sutures 122 extend through holes 112 of holder 102 and through cuff 28 of valve 12 thereby securing holder 102 to valve 12. Hanger 104 includes threaded receptacle 124 and notch 126. Notch 126 is used to suspend hanger 104 from packaging (not shown) during transportation prior to implantation of valve 12. Threaded receptacle 124 is optionally used to receive a threaded handle 125 to facilitate removal of assembly 100 prior to implantation. Handle 125 may also be used in conjunction with assembly 100 to perform a traditional (non-minimally invasive) implantation.

Assembly 100 is used in a minimally invasive manner similar to that described for assembly 10. The surgeon removes the assembly from the packaging (not shown). A handle is inserted into slot 110 of holder 102. Alternatively, the handle 125 may be inserted into assembly 100 before removing assembly 100 from the package. Sutures 120 are cut such that holder 102 may be removed from hanger 104. The minimally invasive implantation procedure proceeds as described above. After valve 12 has been sutured to the patient's heart, sutures 122 are cut and holder 102 is removed.

Figure 5:
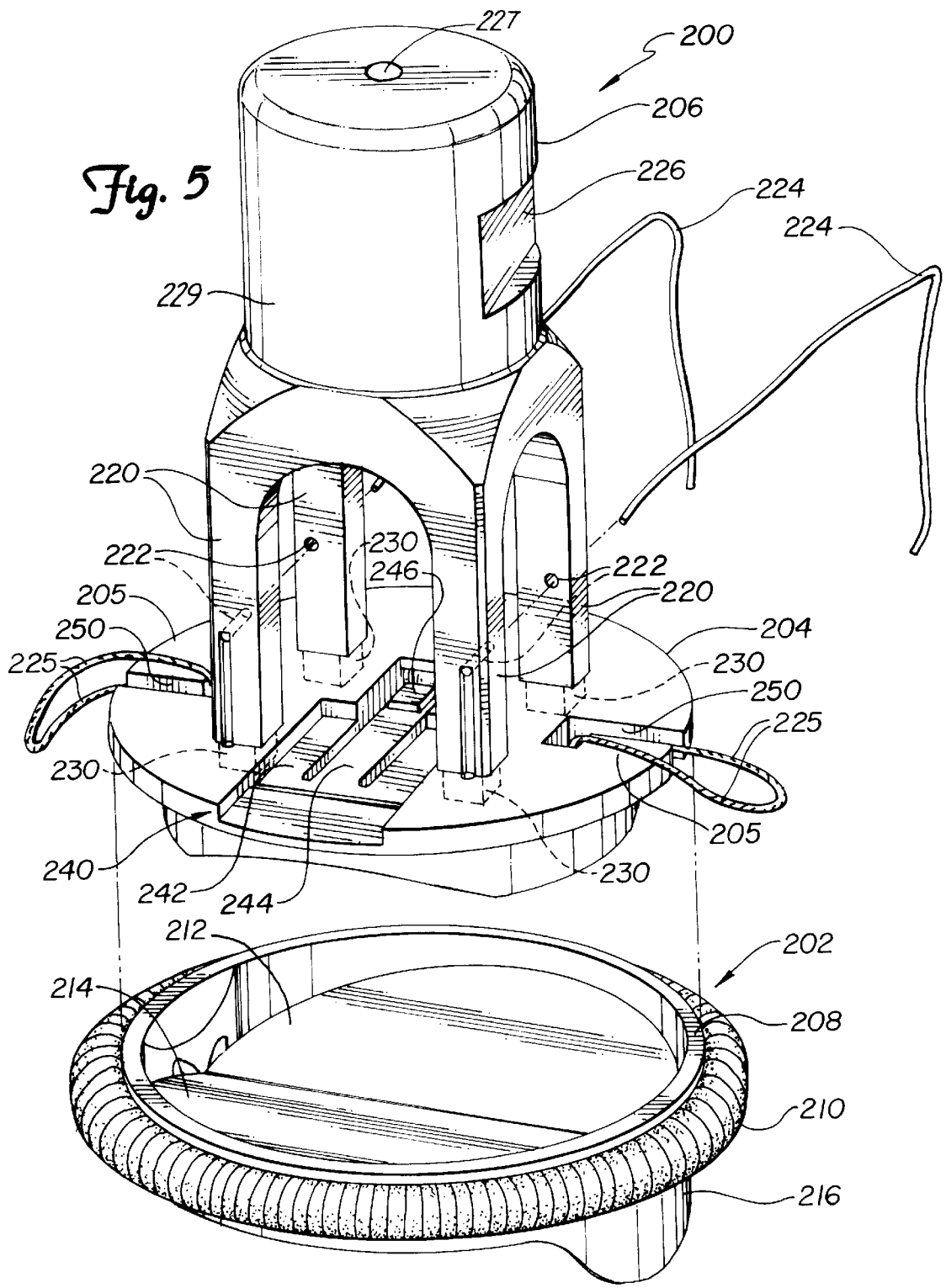
FIG. 5 is a partially exploded perspective view of a hanger and holder in accordance with another embodiment.

FIG. 5 is a perspective partially exploded view of assembly 200 in accordance with another embodiment. Assembly 200 is adapted for use with aortic heart valve prosthesis 202 and includes holder 204 and hanger 206. Aortic valve 202 includes valve orifice 208, cuff 210, leaflets 212 and 214 protected by leaflet pivot guard 216.

Hanger 206 includes hanger legs 220 having suture holes 222 to receive sutures 224. Hanger 206 includes notch 226 adapted for being held in packaging (not shown). A threaded receptacle 227 extends axially into stem 229 of hanger 206 and is adapted for receiving a handle used to facilitate removal of the valve assembly from the package and/or present the valve for a traditional valve replacement surgical procedure.

Holder 204 includes hanger leg receptacles 230 adapted for receiving hanger legs 220 of hanger 206. Hanger 206 is attached to holder 204 with sutures 224 which extend through holes 222 and around holder 204. Holder 204 attaches to valve 202 with sutures 225, shown in more detail in FIG. 5. Holder 204 includes handle receptacle 240 which includes recessed area 242 and cantilever 244 which carries tab 246. Holder 204 is attached to valve 202 by passing a suture 225 through cuff 210. One portion of suture 225 lies within groove 250 and the other portion of suture 225 lies on holder proximal surface 205. The ends of suture 225 are then wrapped around protrusion (not shown) within groove 250 and knotted. The recessed suture opening reduces the likelihood that both ends of suture 225 projecting from cuff 210 are unintentionally severed by the surgeon, thus reducing the possibility of a portion of suture 225 being inadvertently left within the patient's body.

Figure 6:
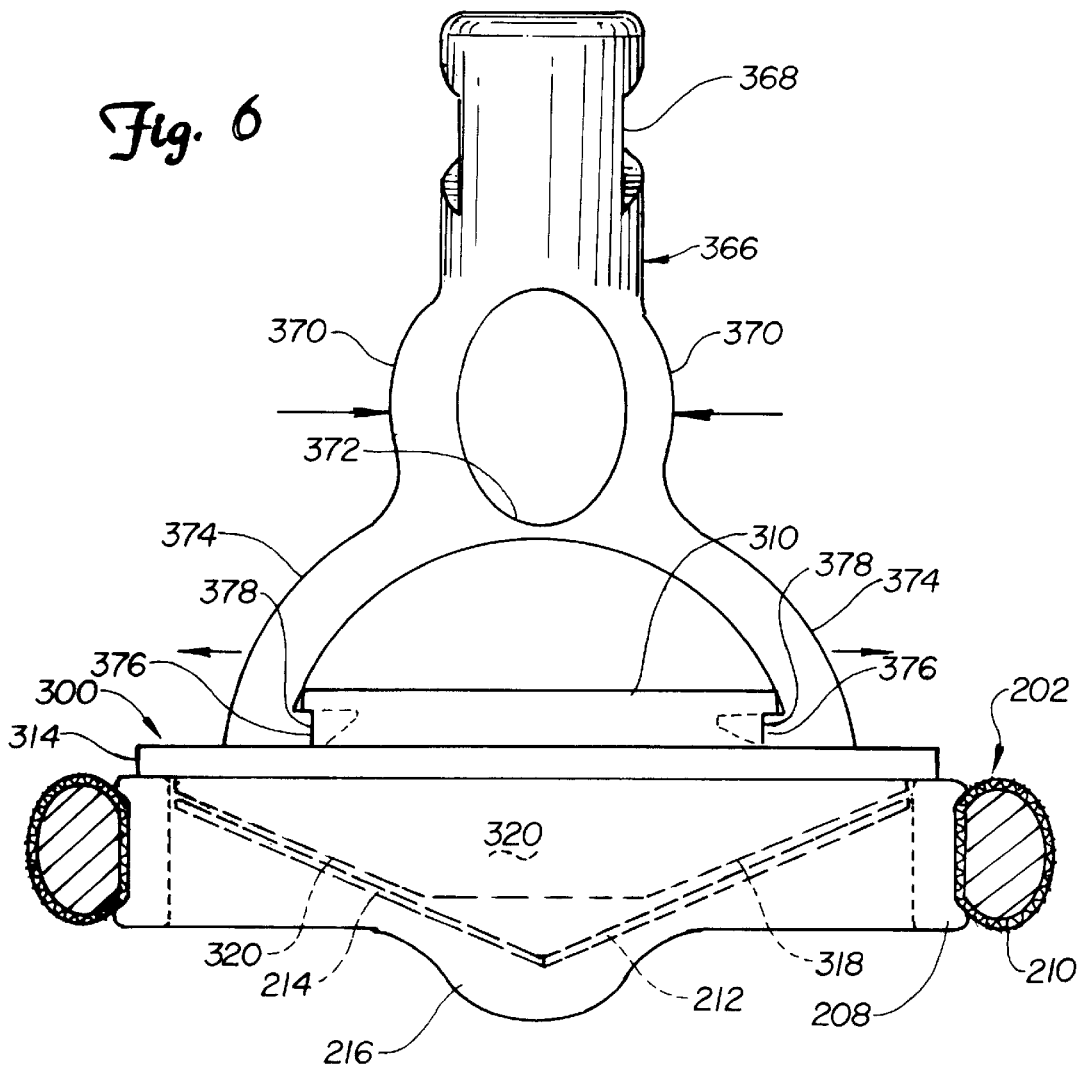
FIG. 6 is a plan view of a hanger adapted for engaging another holder.

FIG. 6 is a plan view of hanger 366 adapted for carrying holder 300, or one or more of the holder embodiments shown herein. For illustrative purposes, valve 202 is shown in cross section. Hanger 366 includes notches 368 adapted for attachment to packaging (not shown), release points 370, pivot 372 and legs 374. Each leg 374 includes tab 376 at its distal end which is adapted to be received in openings 378 of holder 300. Application of pressure to points 370 in the direction shown by the arrows causes legs 374 to spread apart outwardly thereby releasing tabs 376 from openings 378 in holder 300. In one embodiment, a locking member, such as a bar extending between points 370, prevents holder 300 from inadvertently being released from hanger 366 by application of pressure to points 370. Such a locking member can be removed or cut at the appropriate time to allow release of holder 300.

Figure 7A:
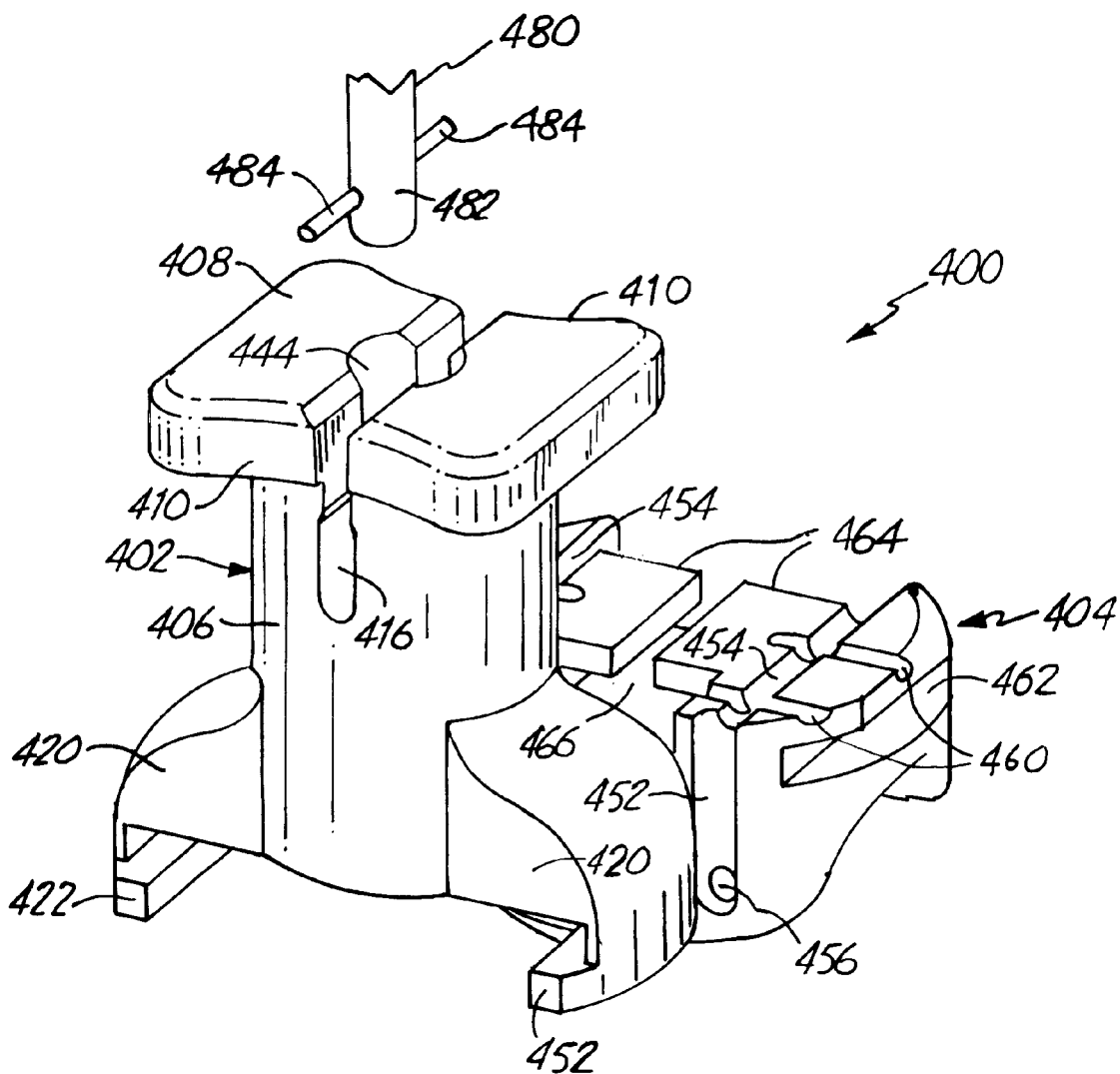
FIG. 7A is a top exploded perspective view of a hanger and holder in accordance with another embodiment.
Figure 7B:
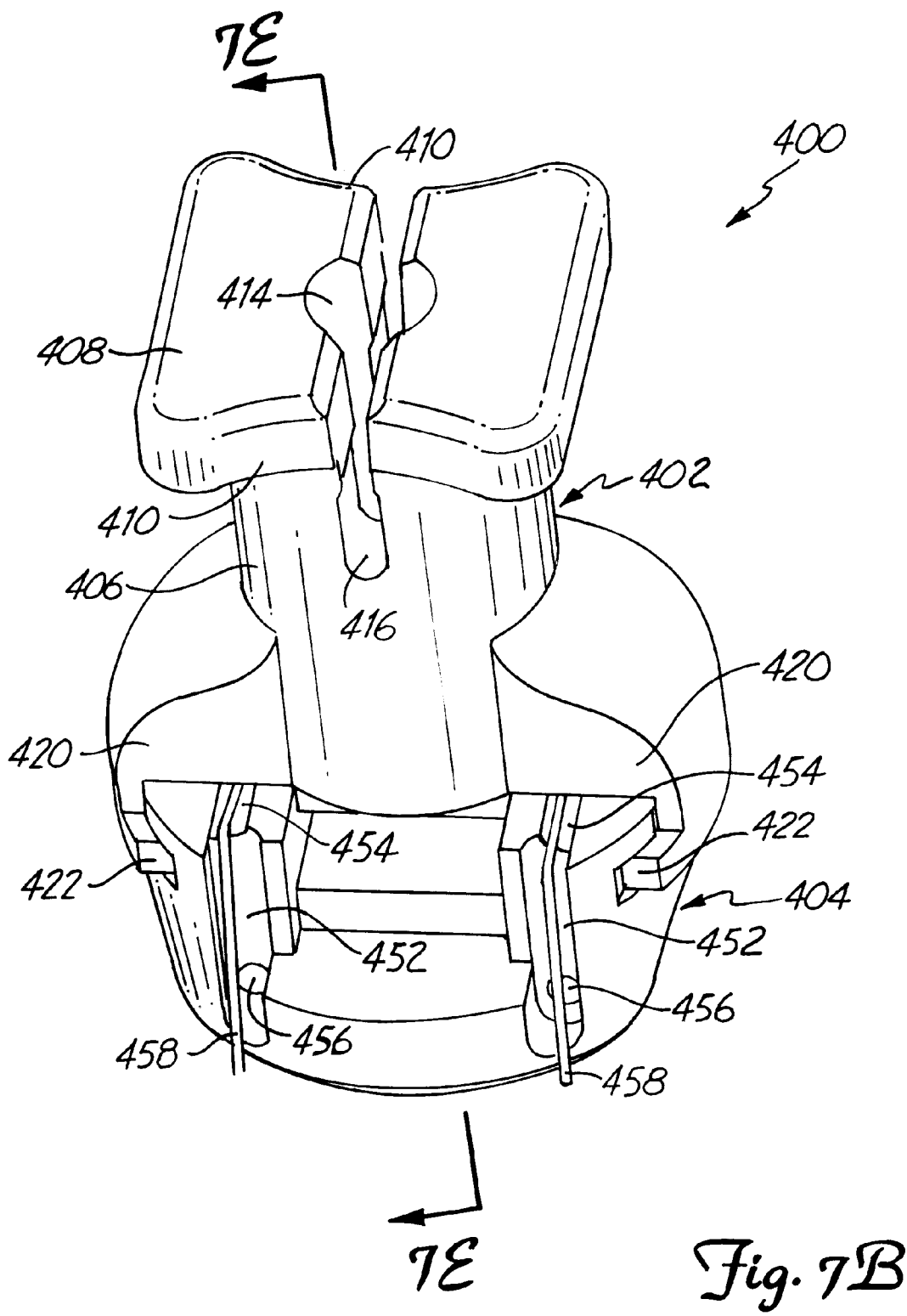
FIG. 7B is a top perspective view of the hanger and holder of FIG. 7A shown coupled to one another.
Figure 7C:
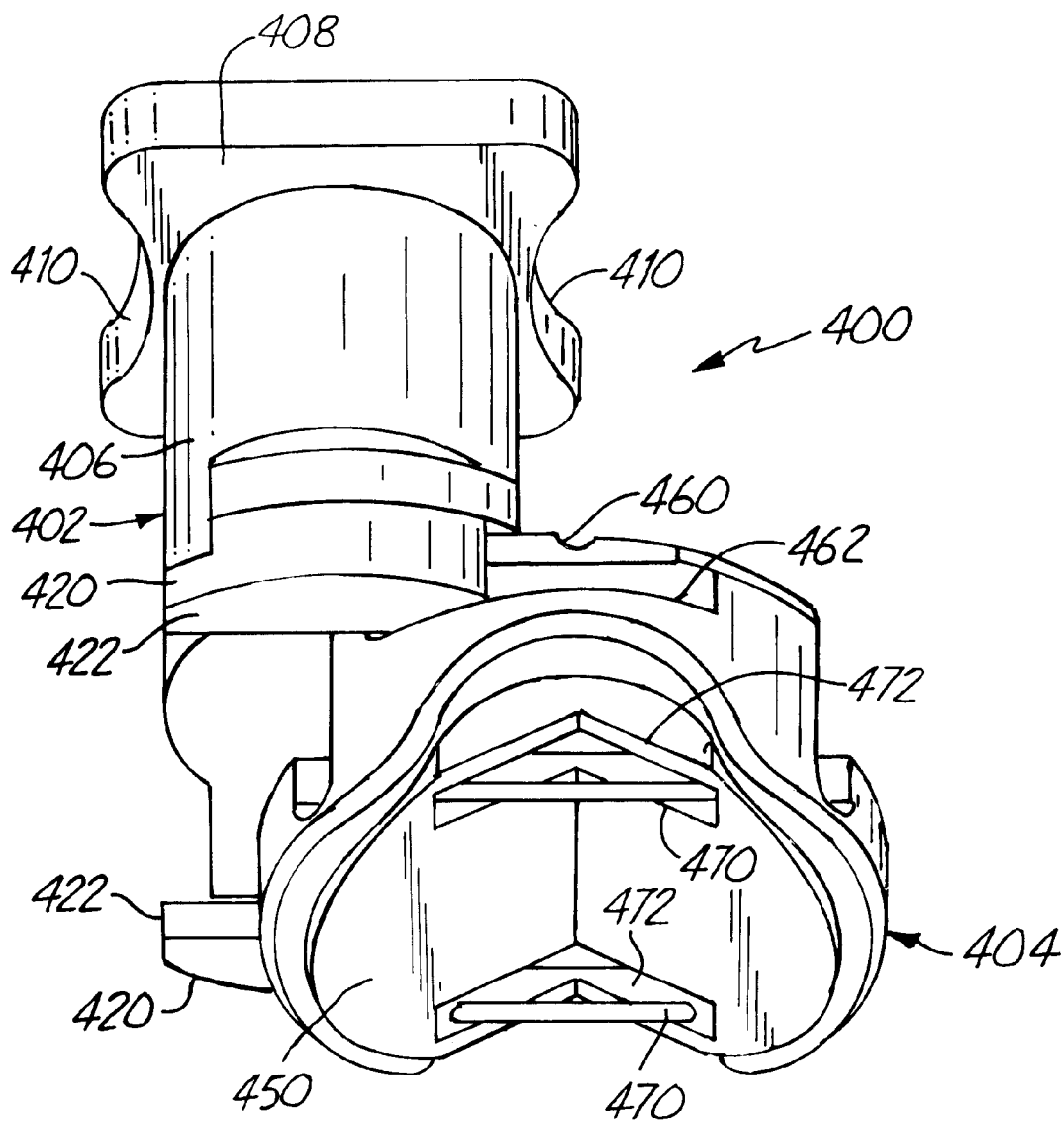
FIG. 7C is a bottom perspective view showing the hanger partially coupled to the holder of FIG. 7A.
Figure 7D:
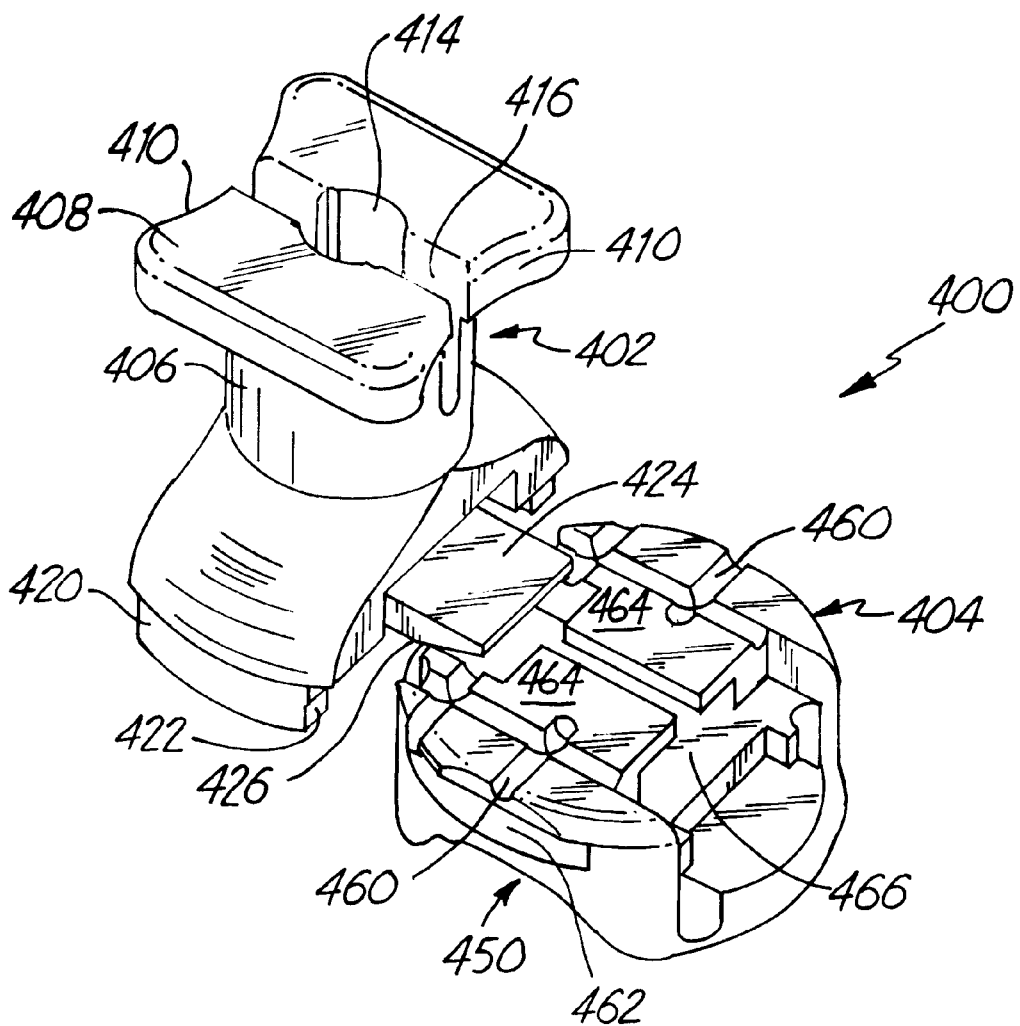
FIG. 7D is a top plan exploded view of the hanger and holder of FIG. 7A.
Figure 7E:
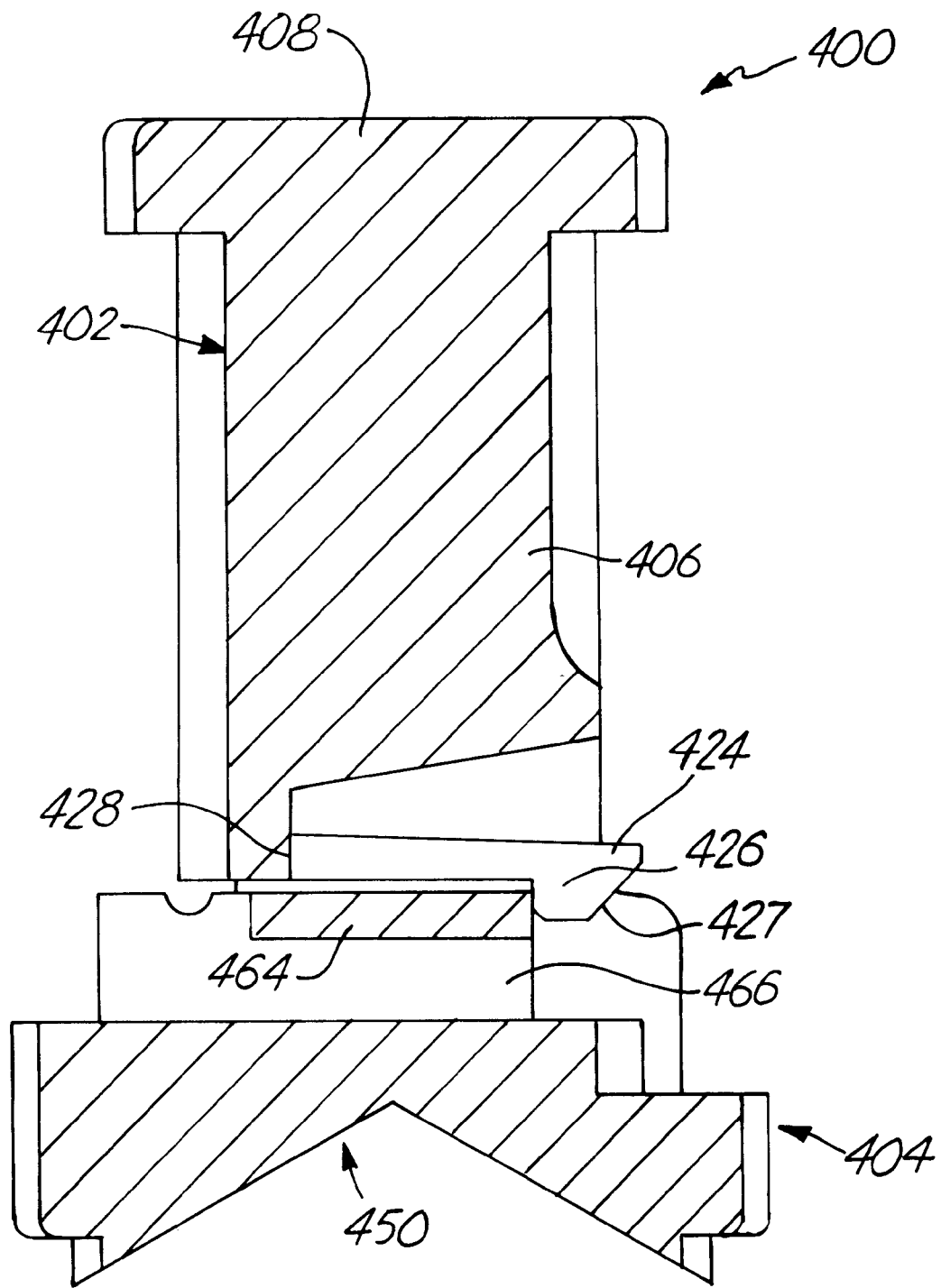
FIG. 7E is a side cross-sectional view of the hanger and holder of FIG. 7B taken along a line labelled 7E—7E.

FIGS. 7A through 7E show an assembly 400 for supporting a mitral heart valve prosthesis (not shown in FIGS. 7A–7E) in accordance with another embodiment. FIG. 7A is an exploded top perspective view of hanger 402 and holder 404 of assembly 400. FIG. 7B is a top perspective view of hanger 402 coupled to holder 404. FIG. 7C is a bottom perspective view of assembly 400 showing hanger 402 partially attached to holder 404. FIG. 7D is a top perspective exploded view of assembly 400. FIG. 7E is a cross-sectional view of assembly 400 taken along line 7E—7E shown in FIG. 7B.

Referring to FIGS. 7A–7E, hanger 402 includes elongated stem 406 which extends in an axial direction relative to the valve prosthesis and includes head portion 408 having finger grip surfaces 410 formed therein, and is used for coupling hanger 402 to packaging. A handle receiving bore 414 is formed in stem 406 and includes slot 416 formed therethrough. Hanger 402 includes legs 420 which carry leg extensions 422. Leg extensions 422 extend inward from legs 420 in a direction generally perpendicular to the axis of stem 406. As shown in the cross-sectional view of FIG. 7E, a cantilever 424 includes tab 426 and couples to stem 406 at attachment point 428.

Holder 404 includes distal engaging surface 450 adapted for engaging a heart valve prosthesis as shown and described above for the other embodiments. It will be understood by those skilled in the art that engaging surface 450 may be modified for us an aortic heart valve prosthesis. Holder 404 includes suture guide grooves 452, suture guide grooves 454 and suture holes 456 for receiving a suture, such as sutures 458 (shown in FIG. 7B) to thereby couple holder 404 to a heart valve prosthesis. Suture cutting grooves 460 are formed in a proximal surface of holder 404 and expose suture 458, thereby allowing suture 458 to be cut with a scalpel, for example, to release the prosthesis from holder 404. Side surfaces of holder 404 include grooves 462 formed therein which are adapted to slidably receive leg extensions 422. The proximal surface of holder 404 also includes tab stops 464 which receive and abut tab 426 as shown in FIG. 7E to thereby lock hanger 402 to holder 404. A handle receiving slot 466 is formed in holder 404 under tab stops 464. Suture holes 456 are also adapted to receive sutures 470 shown in FIG. 7C which extend through suture slots 472 formed in the distal surface 450 of holder 404. Sutures 470 are used to maintain the leaflets of the valve in a substantially closed position during implantation, and may be used to couple holder 404 to the valve prosthesis. Alternative suture 458 and sutures 472 may be the same suture.

As illustrated in FIGS. 7A–7E, hanger 402 is releasably coupled to holder 404. Specifically, leg extensions 422 are slidably received in grooves 462. When leg extensions 422 are slid completely into grooves 462, tab 426 is urged downward by cantilever 424 and into abutting contact with tab stop 464 as cantilever 424 bends or deflects on joint 428. In this position, hanger 402 is secured to holder 404.

Hanger 402 is adapted for traditional (i.e. non-minimally invasive) implantation using, for example, an elongated handle 480 having a shaft 482 and radially extending keys 484 as shown in FIG. 7A. Shaft 482 is adapted for insertion into bore 414 and keys 484 are received in slot 416. A surgeon may use handle 480 to manipulate the heart valve prosthesis during implantation as the prosthesis is moved in a direction generally along the axis of the prosthesis and into the patient. Further, torque may be transmitted from handle 480 to hanger 402 using keys 484 and groove 416 such that the prosthesis may be rotated during the implantation procedure. Additionally, finger grip surfaces 410 may be used by the surgeon to rotate the prosthesis. In the event of a minimally invasive procedure, the handle attached through slot 466 may be used to manipulate and rotate the prosthesis.

Holder 404 may be removed from hanger 402 by disengaging tab 426 from tab stop 464 and slidably removing leg extensions 422 from grooves 462. Slot 466 in holder 404 may receive an elongated handle which extends generally parallel to a plane of the prosthesis such that holder 404 may be used for a minimally invasive implantation procedure.

Figure 8:
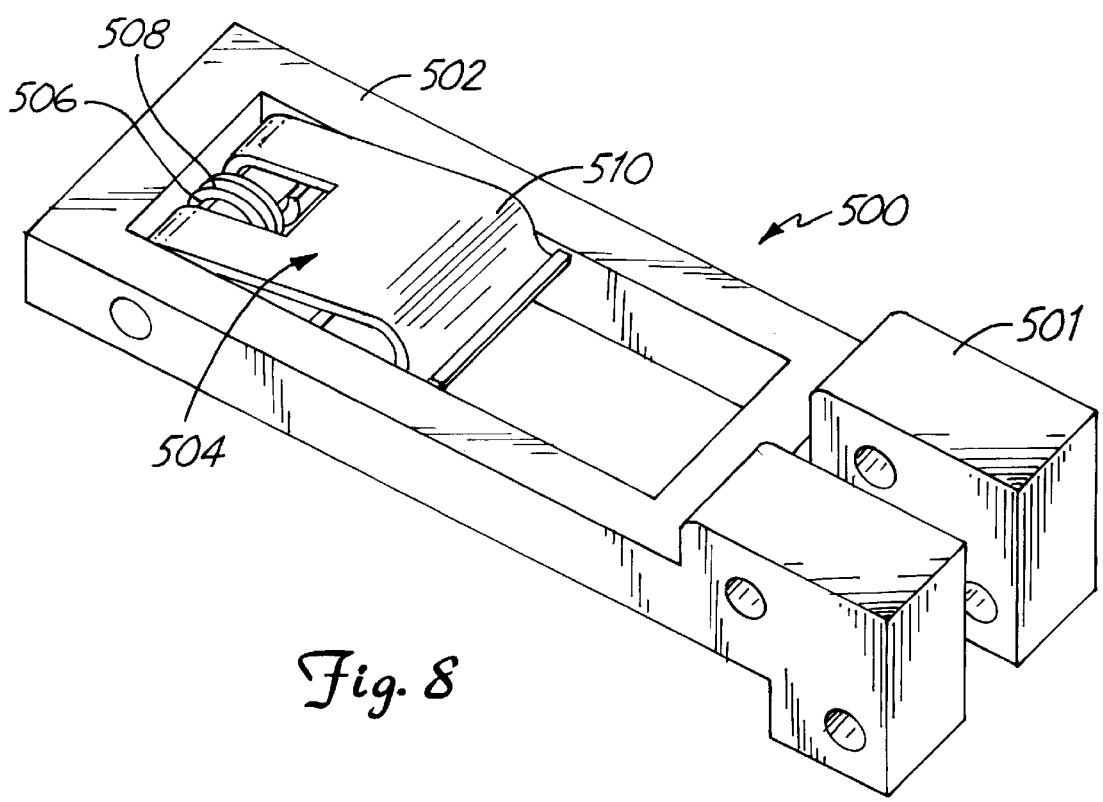
FIG. 8 is a top perspective view of a distal tip of a handle for use with the holder shown in FIGS. 7A–7E.

FIG. 8 is a perspective view of a distal end 500 of one such handle. Distal end 500 includes body portion 502 adapted for being received in slot 466 of holder 404. Distal end 500 includes spring loaded member 504 which is pivotally coupled to axis 506 by spring 508. Spring loaded member 504 provides an engagement mechanism to couple distal end 500 to holder 404 at slot 466. As distal end 500 is inserted into slot 466, edge 501 contacts tab 426 along inclined surface 427 forcing cantilever 424 upward and causing tab 426 to disengage tab stops 464, thereby releasing hanger 402 from holder 404. Thus, it will be apparent that assembly 400 may be used in either a traditional implantation procedure or a minimally invasive procedure.

Figure 9A:
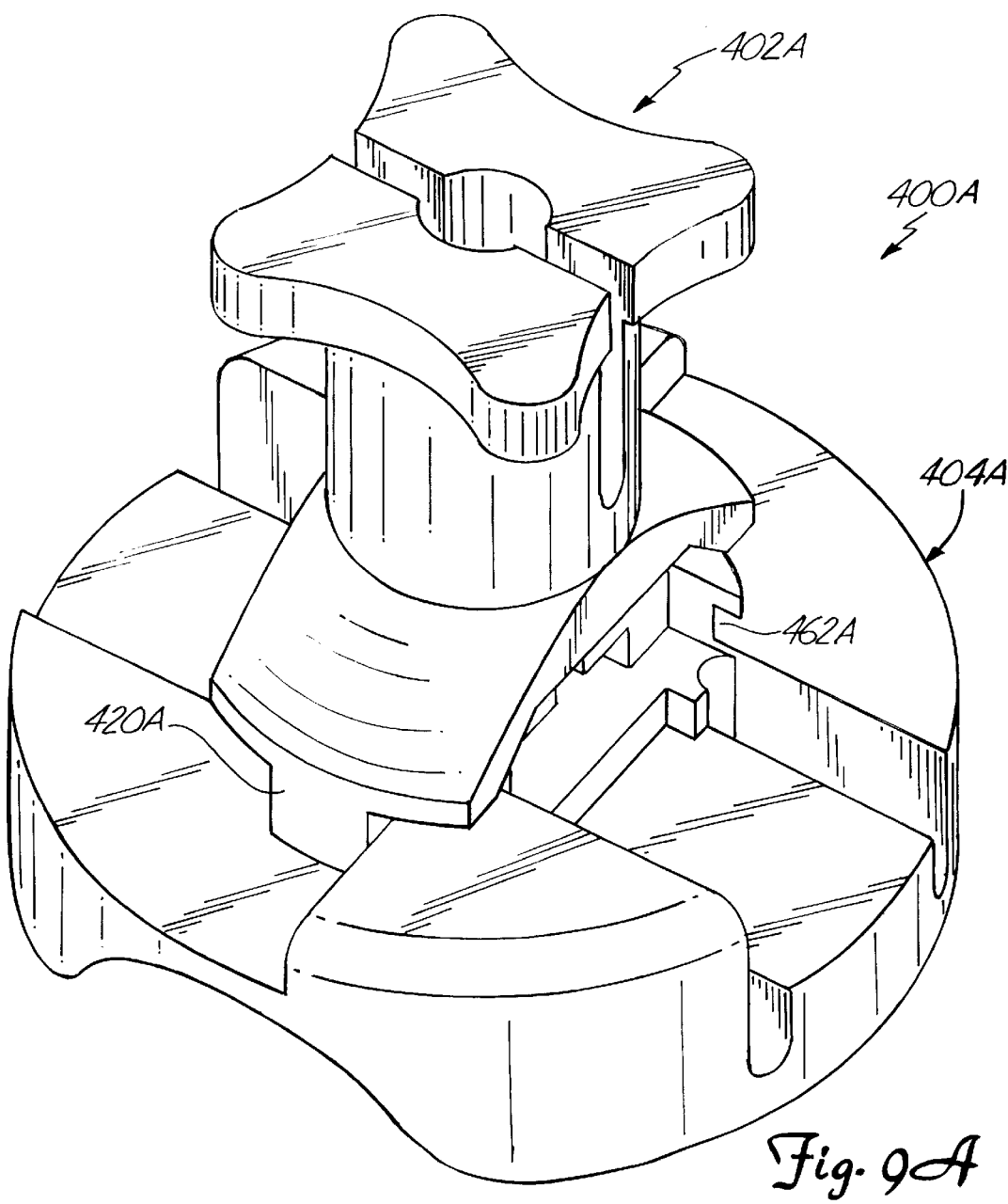
FIGS. 9A and 9B are perspective views of a hanger and holder in accordance with another embodiment.
Figure 9B:
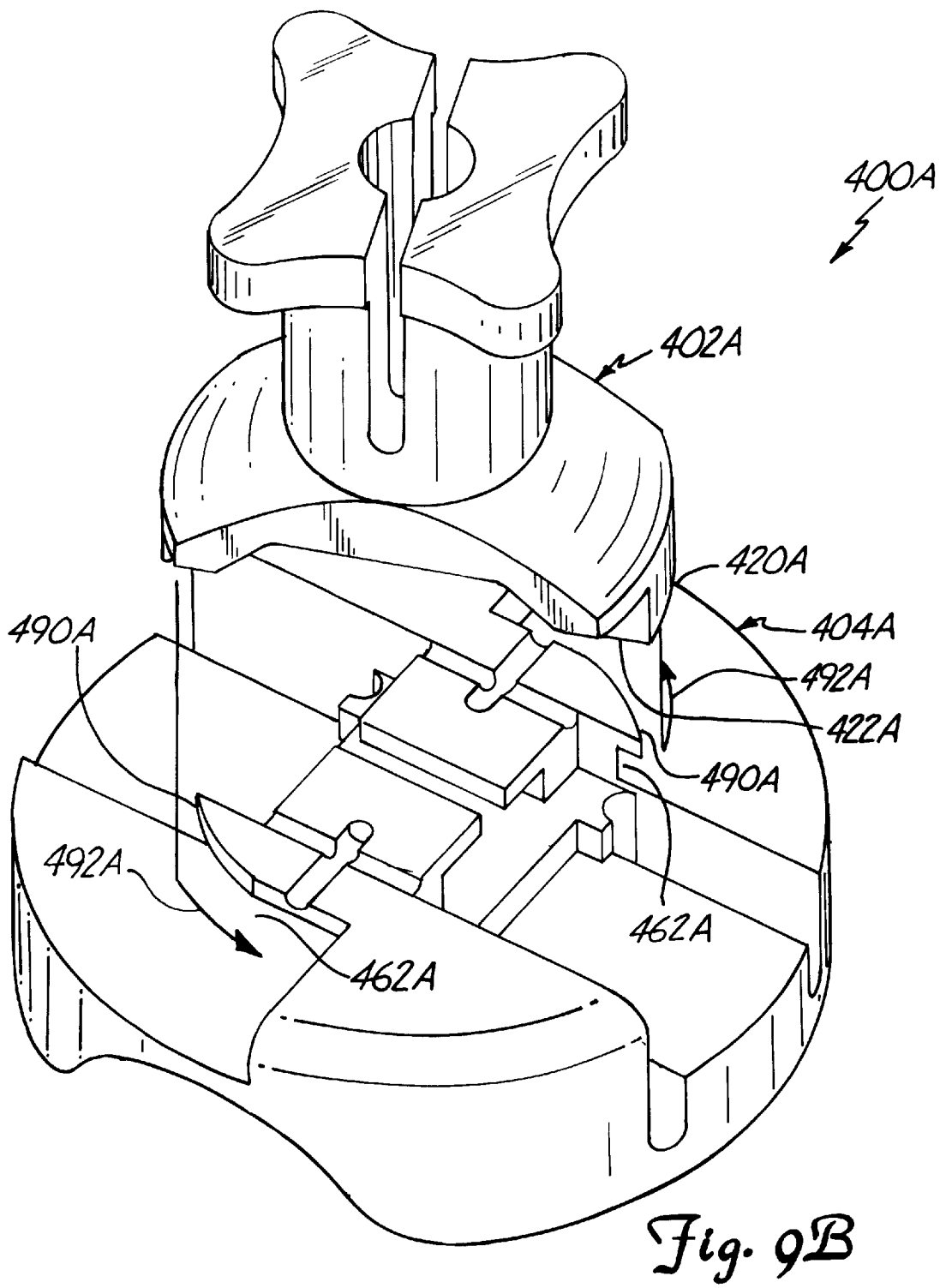

FIGS. 9A and 9B are perspective views of an assembly 400A in accordance with another embodiment. Assembly 400A is similar to assembly 400 as shown in FIGS. 7A–7E except that hanger 402A is removed from holder 404A by rotating hanger 402A relative to holder 404A. Holder 404A includes chamfered walls 490A which define grooves 462A. Grooves 462A are ramped and have a detent such that leg extensions 422A follow the ramp and snap into the detent. FIG. 9A shows hanger 402A attached to holder 404A. FIG. 9B is an exploded view showing hanger 402A spaced apart from holder 404A. Arrows 492A in FIG. 9B show the direction hanger 402A is rotated relative to holder 404A to attach hanger 402A to holder 404A. Similar to the other embodiments described above, assembly 400A can be used for either a traditional implantation through a sternotomy or thoracotomy or a minimally invasive implantation.

Figure 10:
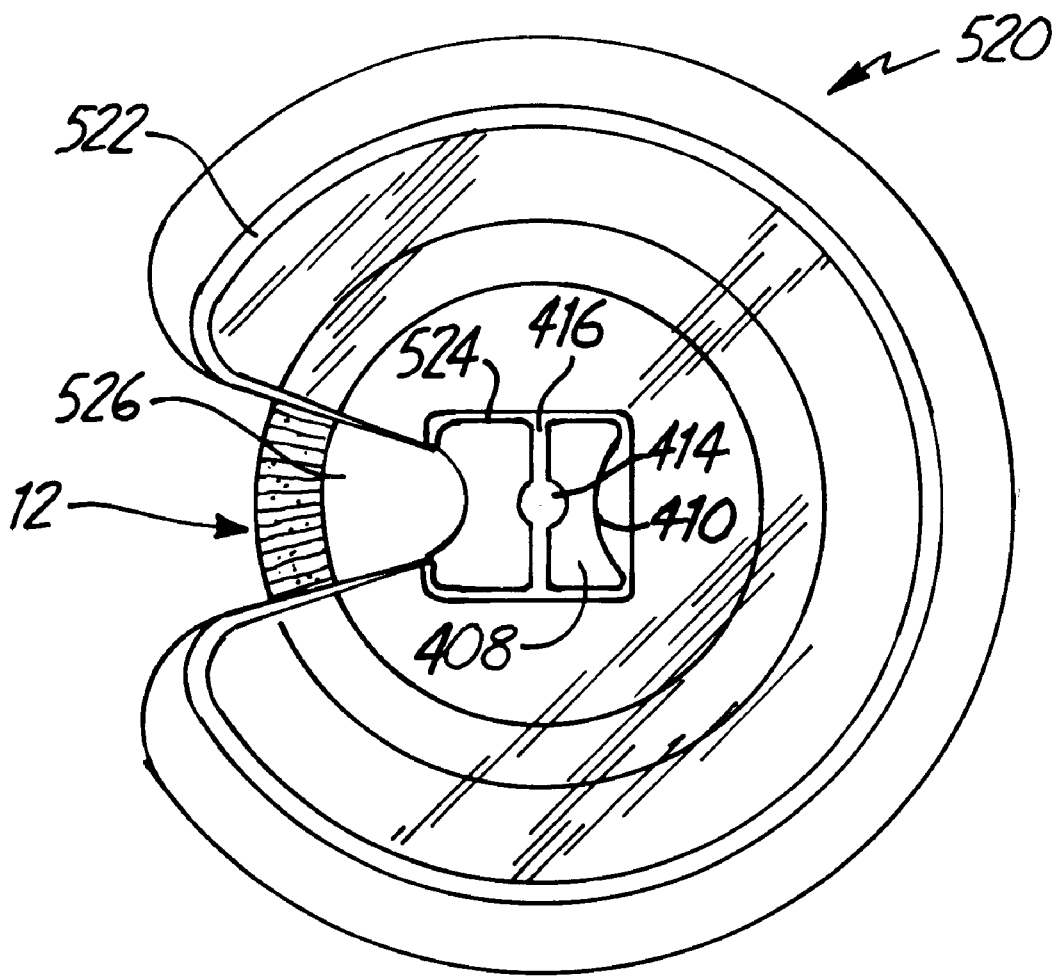
FIG. 10 is a top plan view of packaging for use with the hangers of the present invention.

The above embodiments set forth in FIGS. 7 and 9 have described packaging from which the hanger may be suspended. FIG. 10 is a top plan view of a container top 520 which includes collar 522 formed therein which provides post opening 524. Collar 522 includes hanger receiving opening 526. Head portion 408 is secured in opening 524. Container top 520 is held in a sealed container (not shown). Thus, the hanger/holder/prosthesis assembly may be suspended from container top 520. Additionally, if minimally invasive implantation is to be performed, the holder and prosthesis can be removed from container top 520 while the hanger 402 remains suspended in collar 522.

In general, the materials used herein are materials suited for the biomedical industry. For example, the holder can be made of a polymer such as polyphenylsulfone, known under the trade name of Radel®, or other similar biocompatible durable material, and is suitable for forming by injection molding or other manufacturing methods. Typical materials for the handle include stainless steel, or other biocompatible metals or polymers. Additionally, all designs tend to allow easy attachment of the handle to the holder during surgery while maintaining the sterile condition of the pieces. Injection molding techniques are well suited for fabricating the low profile holder set forth herein. A suitable distance between a leaflet and a leaflet engaging surface is maintained so as to not apply pressure to the leaflets during transportation or use of the valve while attached to the low profile holder. This stabilizes the leaflet without substantial contact to the leaflet which could damage the leaflet. Additional soft padding material may be carried on the leaflet engaging surface. Furthermore, the holder set forth herein provides a pivot guard to prevent the handle from contacting the valve during use.

The hanger and holder of the invention allow the low profile holder to couple to existing packaging. Further, the hanger may remain coupled to the holder such that the assembly may be used in a traditional (non-minimally invasive) implantation procedure. Further, "coupling area" is hereby defined as any area of the holder which is used to couple the holder to the hanger. The various holders and hangers may be used with either aortic or mitral valves. All hangers shown herein may be used with the packaging of FIG. 10, or with other appropriate packaging with minor modifications.

The invention as set forth herein securely attaches the holder to the valve and the holder to the handle or hanger as one integral piece. The low profile design allows easy and safe manipulation of the valve in a surgical environment and during implantation. Easy engagement (and disengagement) of the holder and handle assembly is provided which has advantages including speed, ease of use, safety and effectiveness in a surgical environment. The integral packaging allows the entire assembly to be sterilized as a unit. The various elements are provided for easy manufacture using injection molding techniques. Protection of the leaflets within the valve orifice is maintained and the low profile allows minimally invasive surgical techniques. Further, those skilled in the art will recognize that the invention may be used with a type of handle or handles with simple modifications. The invention is in no way limited to the particular handles or configurations set forth herein.

Although the present invention has been described with reference to preferred embodiments, workers skilled in the art will recognize that changes may be made in form and detail without departing from the spirit and scope of the invention, including use of the hanger with holders for bioprosthetic valves and annuloplasty rings.

What is claimed is:

1. An apparatus for supporting a heart valve prosthesis having an annulus, comprising:
   a low profile holder having a distal engaging surface adapted for independent coupling to the heart valve prosthesis;
   a coupling area comprising a groove extending generally parallel with a plane of the annulus of the prosthesis defined in the low profile holder, and wherein the plane is generally perpendicular to an axis of the annulus; and
   a hanger having a proximal end adapted for suspension from packaging and a distal end having a leg providing a leg extension which is adapted to be received in the groove for selectively coupling to the coupling area whereby the hanger is removably coupled to the low profile holder by sliding the leg into the coupling area in a direction generally parallel with the plane of the annulus.

2. The apparatus of claim 1 wherein the low profile holder includes an opposing groove defined therein opposite the groove, and the hanger includes an opposing leg opposite the leg generally conforming to the opposing groove whereby the legs grasp the low profile hanger at the grooves.

3. The apparatus of claim 1 wherein the hanger includes a moveable tab and the low profile holder includes a tab stop adapted for receiving the moveable tab to thereby prevent the hanger from sliding relative to the low profile holder.

4. The apparatus of claim 1 wherein the hanger includes first and second opposed stems carrying respective first and second opposed legs which are adapted to couple to the coupling area of the low profile holder.

5. The apparatus of claim 4 wherein the stems provide relative movement about a pivot to thereby spread the legs and release the low profile holder.

6. The apparatus of claim 5 wherein the pivot joins, the first and second stems and the relative movement occurs by bending the pivot.

7. The apparatus of claim 4 including a removable collar extending around the stems to thereby releaseably secure the stems together.

8. The apparatus of claim 1 wherein the proximal end of the holder is adapted to couple to an elongated handle.

9. The apparatus of claim 8 wherein coupling of the handle to the prosthesis through the hanger and the holder is of sufficient strength to allow a torque to be applied to the prosthesis by the handle.

10. The apparatus of claim 1 wherein the holder is adapted to receive a handle which extends in a direction generally perpendicular to a plane defined by the annulus of the prosthesis for use in a minimally invasive implantation procedure.

11. An apparatus for supporting a heart valve prosthesis having an annulus, comprising:
    a low profile holder adapted for independent coupling to the heart valve holder and including a groove defined therein extending generally parallel with a plane of the annulus, wherein the plane is perpendicular to an axis of the annulus of the prosthesis;
    a hanger having a distal end which includes a leg having a leg extension adapted to be slidably coupled to the low profile holder at the groove by sliding in a direction substantially parallel with the plane; and
    wherein the hanger includes a moveable tab and the low profile holder includes a tab stop adapted for receiving the moveable tab to thereby prevent the hanger from sliding relative to the low profile holder.

12. The apparatus of claim 11 wherein the low holder includes an opposing groove defined therein opposite the groove, and the hanger includes an opposing leg opposite the leg generally conforming to the opposing groove whereby the legs grasp the low profile hanger at the grooves.

13. The apparatus of claim 11 wherein the proximal end of the holder is adapted to couple to an elongated handle.

14. The apparatus of claim 13 wherein coupling of the handle to the prosthesis through the hanger and the holder is of sufficient strength to allow a torque to be applied to the prosthesis by the handle.

15. The apparatus of claim 11 wherein the holder is adapted to receive a handle which extends in a direction generally perpendicular to a plane defined by the annulus of the prosthesis for use in a minimally invasive implantation procedure.

16. An apparatus for supporting a heart valve prosthesis having an annulus, comprising:

a low profile holder adapted for independent coupling to the heart valve holder and including a groove defined therein extending generally parallel with a plane of the annulus, wherein the plane is perpendicular to an axis of the annulus of the prosthesis;

a hanger having a distal end which includes a leg having a leg extension adapted to be slidably coupled to the low profile holder at the groove by sliding in a direction substantially perpendicular to the plane; and wherein the holder is adapted to receive a handle which extends in a direction generally perpendicular to a plane defined by the annulus of the prosthesis for use in a minimally invasive implantation procedure, and the hanger includes a moveable tab and the low profile holder includes a tab stop adapted for receiving the moveable tab to thereby prevent the hanger from sliding relative to the low profile holder.

17. The apparatus of claim 16 wherein the low profile holder includes an opposing groove defined therein opposite the groove, and the hanger includes an opposing leg opposite the leg generally conforming to the opposing groove whereby the legs grasp the low profile hanger at the grooves.

18. The apparatus of claim 16 wherein the proximal end of the holder is adapted to couple to an elongated handle.

19. The apparatus of claim 16 wherein coupling of the handle to the prosthesis through the hanger and the holder is of sufficient strength to allow a torque to be applied to the prothesis by the handle.

* * * * *

UNITED STATES PATENT AND TRADEMARK OFFICE
CERTIFICATE OF CORRECTION

PATENT NO.    : 6,214,043 B1
DATED         : April 10, 2001
INVENTOR(S)   : Kurt D. Krueger It is certified that error appears in the above-identified patent and that said Letters Patent is hereby corrected as shown below:

Title page,
Item [75], Inventors, delete "Kimberly A. Anderson, Eagan;" and "Thomas F. Hinnenkamp, White Bear Lake".

Column 8,
Line 52, after "low" insert -- profile --.

Signed and Sealed this

Thirteenth Day of August, 2002

Attest:

JAMES E. ROGAN
*Attesting Officer*          *Director of the United States Patent and Trademark Office*